US010750931B2

(12) United States Patent
Begg

(10) Patent No.: US 10,750,931 B2
(45) Date of Patent: Aug. 25, 2020

(54) SYSTEMS AND METHODS FOR GENERATING A FLUID BEARING FOR AN OPERATIVE PROCEDURE

(71) Applicant: COVIDIEN LP, Mansfield, MA (US)

(72) Inventor: Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 15/572,865

(22) PCT Filed: May 24, 2016

(86) PCT No.: PCT/US2016/033921
§ 371 (c)(1),
(2) Date: Nov. 9, 2017

(87) PCT Pub. No.: WO2016/191422
PCT Pub. Date: Dec. 1, 2016

(65) Prior Publication Data
US 2018/0153376 A1 Jun. 7, 2018

Related U.S. Application Data

(60) Provisional application No. 62/166,479, filed on May 26, 2015.

(51) Int. Cl.
A61B 1/00 (2006.01)
A61B 1/015 (2006.01)
A61B 1/313 (2006.01)
A61B 1/317 (2006.01)

(52) U.S. Cl.
CPC ...... *A61B 1/00091* (2013.01); *A61B 1/00135* (2013.01); *A61B 1/015* (2013.01); *A61B 1/313* (2013.01); *A61B 1/317* (2013.01); *A61B 1/00096* (2013.01)

(58) Field of Classification Search
None
See application file for complete search history.

(56) References Cited

U.S. PATENT DOCUMENTS

| 1,585,934 A | 5/1926 | Muir |
| 1,666,332 A | 4/1928 | Hirsch |
| 1,831,786 A | 11/1931 | Duncan |
| 2,708,437 A | 5/1955 | Hutchins |

(Continued)

FOREIGN PATENT DOCUMENTS

| JP | H05-285094 A | 11/1993 |
| JP | H06-181879 A | 7/1994 |
| WO | 94-05200 A1 | 3/1994 |

*Primary Examiner* — Timothy J Neal
(74) *Attorney, Agent, or Firm* — Carter, DeLuca & Farrell LLP

(57) ABSTRACT

Systems and methods discussed herein are related to the formation of a fluid bearing between an interior surface of an aperture and an outside surface of an endoscopic device. The fluid bearing is formed via various fluid paths created in an annular space between an inside surface of a sheath and an outside surface of an endoscope telescoped within the sheath. The fluid bearing reduces the friction between the interior surface of an aperture and the outside surface of an endoscopic device by allowing the interior surface of the aperture to rest on the fluid bearing during insertion of a portion of the distal tip of the endoscopic device.

15 Claims, 13 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,850,162 A | 11/1974 | Iglesias |
| 3,900,022 A | 8/1975 | Widran |
| 3,939,839 A | 2/1976 | Curtiss |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,423,727 A | 1/1984 | Widran et al. |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,191,878 A | 3/1993 | Iida et al. |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,257,617 A | 11/1993 | Takahashi |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,637,075 A | 6/1997 | Kikawada |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |

(56) References Cited

U.S. PATENT DOCUMENTS

| | | | |
|---|---|---|---|
| 5,928,163 | A | 7/1999 | Roberts et al. |
| 5,944,654 | A | 8/1999 | Crawford |
| 5,944,668 | A | 8/1999 | Vancaillie et al. |
| 5,947,990 | A | 9/1999 | Smith |
| 5,951,490 | A | 9/1999 | Fowler |
| 5,956,130 | A | 9/1999 | Vancaillie et al. |
| 5,957,832 | A | 9/1999 | Taylor et al. |
| 6,001,116 | A | 12/1999 | Heisler et al. |
| 6,004,320 | A | 12/1999 | Casscells et al. |
| 6,007,513 | A | 12/1999 | Anis et al. |
| 6,024,751 | A | 2/2000 | Lovato et al. |
| 6,032,673 | A | 3/2000 | Savage et al. |
| 6,039,748 | A | 3/2000 | Savage et al. |
| 6,042,552 | A | 3/2000 | Cornier |
| 6,068,641 | A | 5/2000 | Varsseveld |
| 6,086,542 | A | 7/2000 | Glowa et al. |
| 6,090,123 | A | 7/2000 | Culp et al. |
| 6,113,594 | A | 9/2000 | Savage |
| 6,119,973 | A | 9/2000 | Galloway |
| 6,120,147 | A | 9/2000 | Vijfvinkel et al. |
| 6,120,462 | A | 9/2000 | Hibner et al. |
| 6,132,369 | A | 10/2000 | Takahashi |
| 6,132,448 | A | 10/2000 | Perez et al. |
| 6,149,633 | A | 11/2000 | Maaskamp |
| 6,156,049 | A | 12/2000 | Lovato et al. |
| 6,159,160 | A | 12/2000 | Hsei et al. |
| 6,159,209 | A | 12/2000 | Hakky |
| 6,203,518 | B1 | 3/2001 | Anis et al. |
| 6,217,543 | B1 | 4/2001 | Anis et al. |
| 6,224,603 | B1 | 5/2001 | Marino |
| 6,244,228 | B1 | 6/2001 | Kuhn et al. |
| 6,258,111 | B1 | 7/2001 | Ross et al. |
| 6,277,096 | B1 | 8/2001 | Cortella et al. |
| 6,315,714 | B1 | 11/2001 | Akiba |
| 6,358,200 | B1 | 3/2002 | Grossi |
| 6,358,263 | B2 | 3/2002 | Mark et al. |
| 6,359,200 | B1 | 3/2002 | Day |
| 6,402,701 | B1 | 6/2002 | Kaplan et al. |
| 6,428,486 | B2 | 8/2002 | Ritchart et al. |
| 6,471,639 | B2 | 10/2002 | Rudischhauser et al. |
| 6,494,892 | B1 | 12/2002 | Ireland et al. |
| 6,585,708 | B1 | 7/2003 | Maaskamp |
| 6,610,066 | B2 | 8/2003 | Dinger et al. |
| 6,626,827 | B1 | 9/2003 | Felix et al. |
| 6,632,182 | B1 | 10/2003 | Treat |
| 6,656,132 | B1 | 12/2003 | Ouchi |
| 6,712,773 | B1 | 3/2004 | Viola |
| 6,837,847 | B2 | 1/2005 | Ewers et al. |
| 7,025,732 | B2 | 4/2006 | Thompson et al. |
| 7,150,713 | B2 | 12/2006 | Shener et al. |
| 7,226,459 | B2 | 6/2007 | Cesarini et al. |
| 7,249,602 | B1 | 7/2007 | Emanuel |
| 7,510,563 | B2 | 3/2009 | Cesarini et al. |
| 7,763,033 | B2 | 7/2010 | Gruber et al. |
| 7,922,737 | B1 | 4/2011 | Cesarini et al. |
| 8,061,359 | B2 | 11/2011 | Emanuel |
| 9,226,650 | B2 | 1/2016 | Emanuel |
| 2001/0039963 | A1 | 11/2001 | Spear et al. |
| 2001/0047183 | A1 | 11/2001 | Privitera et al. |
| 2002/0058859 | A1 | 5/2002 | Brommersma |
| 2003/0050603 | A1 | 3/2003 | Todd |
| 2003/0050638 | A1 | 3/2003 | Yachia et al. |
| 2003/0078609 | A1 | 4/2003 | Finlay et al. |
| 2003/0114875 | A1 | 6/2003 | Sjostrom |
| 2003/0130565 | A1 | 7/2003 | Muller |
| 2004/0204671 | A1 | 10/2004 | Stubbs et al. |
| 2005/0043690 | A1 | 2/2005 | Todd |
| 2005/0085692 | A1 | 4/2005 | Kiehn et al. |
| 2005/0085695 | A1* | 4/2005 | Shener ............ A61B 1/00071 600/156 |
| 2006/0036132 | A1 | 2/2006 | Renner et al. |
| 2006/0047185 | A1 | 3/2006 | Shener et al. |
| 2006/0241586 | A1 | 10/2006 | Wilk |
| 2007/0027359 | A1* | 2/2007 | Salman ............ A61B 1/00135 600/121 |
| 2008/0015621 | A1 | 1/2008 | Emanuel |
| 2008/0058588 | A1 | 3/2008 | Emanuel |
| 2008/0058842 | A1 | 3/2008 | Emanuel |
| 2008/0097468 | A1 | 4/2008 | Adams et al. |
| 2008/0097469 | A1 | 4/2008 | Gruber et al. |
| 2008/0097470 | A1 | 4/2008 | Gruber et al. |
| 2008/0097471 | A1 | 4/2008 | Adams et al. |
| 2008/0135053 | A1 | 6/2008 | Gruber et al. |
| 2008/0146872 | A1 | 6/2008 | Gruber et al. |
| 2008/0146873 | A1 | 6/2008 | Adams et al. |
| 2008/0245371 | A1 | 10/2008 | Gruber |
| 2008/0249366 | A1 | 10/2008 | Gruber et al. |
| 2008/0249534 | A1 | 10/2008 | Gruber et al. |
| 2008/0249553 | A1 | 10/2008 | Gruber et al. |
| 2008/0262308 | A1 | 10/2008 | Prestezog et al. |
| 2009/0270812 | A1 | 10/2009 | Litscher et al. |
| 2009/0270895 | A1 | 10/2009 | Churchill et al. |
| 2009/0270896 | A1 | 10/2009 | Sullivan et al. |
| 2009/0270897 | A1 | 10/2009 | Adams et al. |
| 2009/0270898 | A1 | 10/2009 | Chin et al. |
| 2010/0087798 | A1 | 4/2010 | Adams et al. |
| 2010/0152647 | A1 | 6/2010 | Shener et al. |
| 2012/0041265 | A1* | 2/2012 | Kucklick ............ A61M 1/0084 600/125 |
| 2014/0378771 | A1 | 12/2014 | St. Onge et al. |

\* cited by examiner

SYSTEMS AND METHODS FOR GENERATING A FLUID BEARING FOR AN OPERATIVE PROCEDURE

CROSS-REFERENCE TO RELATED APPLICATIONS

This application is a U.S. National Stage Application under 35 U.S.C. § 371(a) of PCT/US2016/033921 filed May 24, 2016, which claims the benefit of U.S. Provisional Application No. 62/166,479 titled "Endoscope Insertion Assisted by Fluid Bearing Effect," filed May 26, 2015. Each of these applications is hereby incorporated by reference herein as if reproduced in full below.

BACKGROUND

Medical endoscopes are inserted axially into the patient through a small orifice, incision, or other entry point, often using significant force to first expand the constriction and then overcome sliding friction between the orifice and the outer surface of the endoscope as it is advanced further. The difficulty in insertion often causes discomfort and trauma for the patient and frustration for the clinician. In many applications, the critical dimension of the orifice is smaller than the diameter of the endoscope cross-section, which means the orifice expands to accommodate the endoscope. Depending on the tissue structure, mechanical properties, and proximity to nerves, the deformation caused by insertion of the endoscope may result in tissue trauma and pain.

To reduce pain, many times the diameter of the endoscope is reduced; however, the diameter must be large enough to contain the functional components of the endoscope, and as such the diameter is often practically limited and other methods of reducing tissue trauma and pain may be developed.

SUMMARY

In an embodiment, a method of performing a surgical procedure, comprising: positioning a distal tip of a endoscopic device to abut an aperture into an operative cavity, the endoscopic device defines perforations disposed along a length of a first portion of a distal end of the endoscopic device, and the perforations in fluid communication with a fluid path within the endoscopic device; forming a fluid bearing between an inside surface of the aperture and an outside surface of the distal end of the endoscopic device by: establishing a fluid flow along the fluid path and through the perforations; and inserting at least the first portion of the distal tip of the endoscopic device through the aperture as the fluid flows through the perforations.

In an embodiment, a system comprising: a sheath comprising an elongate shaft that defines a central axis, a proximal end, a distal end; an endoscope telescoped at least partially within the sheath to form an endoscope-sheath combination, the endoscope defines a working channel and an optical channel along a length of the endoscope; a view port defined on a proximal end of the endoscope; a visualization conduit that extends through the optical channel and into the view port; a fluid path defined by an annular space between an interior surface of the sheath and an exterior surface of the endoscope telescoped within the sheath; a fluid port defined on the proximal end of the sheath, the fluid port in fluid communication with the fluid path, and the fluid port fluidly coupled to a discharge port of a fluid pump; and a means for establishing a fluid bearing during insertion of the endoscope-sheath combination into an aperture, the means for establishing the fluid bearing defined on the distal end of the endoscope-sheath combination.

A method of performing a surgical procedure, comprising: positioning a distal tip of a endoscopic device to abut an aperture into a patient's body, the endoscopic device defines perforations disposed along a length of a first portion of a distal end of the endoscopic device, and the perforations in fluid communication with a fluid path within the endoscopic device; forming a fluid bearing between an inside surface of the aperture and an outside surface of the distal end of the endoscopic device, the forming by: establishing a fluid flow along the fluid path and through the perforations; and inserting at least the first portion of the distal tip of the endoscopic device through the aperture as the fluid flows through the perforations.

A method comprising: positioning a distal tip of a endoscopic device to abut an aperture into an operative cavity, the endoscopic device comprises an endoscope telescoped within a sheath, the endoscope and sheath define a fluid path along an annular space between an interior surface of the sheath and an exterior surface of the endoscope, and the endoscope and sheath define a discharge outlet circumscribing the endoscope at a distal tip of the sheath; forming a fluid bearing between an inside surface of the aperture and an outside surface of the endoscopic device by: establishing a fluid flow along the fluid path and out through the discharge outlet; and inserting at least a first portion of the distal end of the endoscopic device through the aperture as the fluid flows through the discharge outlet.

BRIEF DESCRIPTION OF THE DRAWINGS

For a detailed description of exemplary embodiments, reference will now be made to the accompanying drawings in which.

DEFINITIONS

Figure 1:
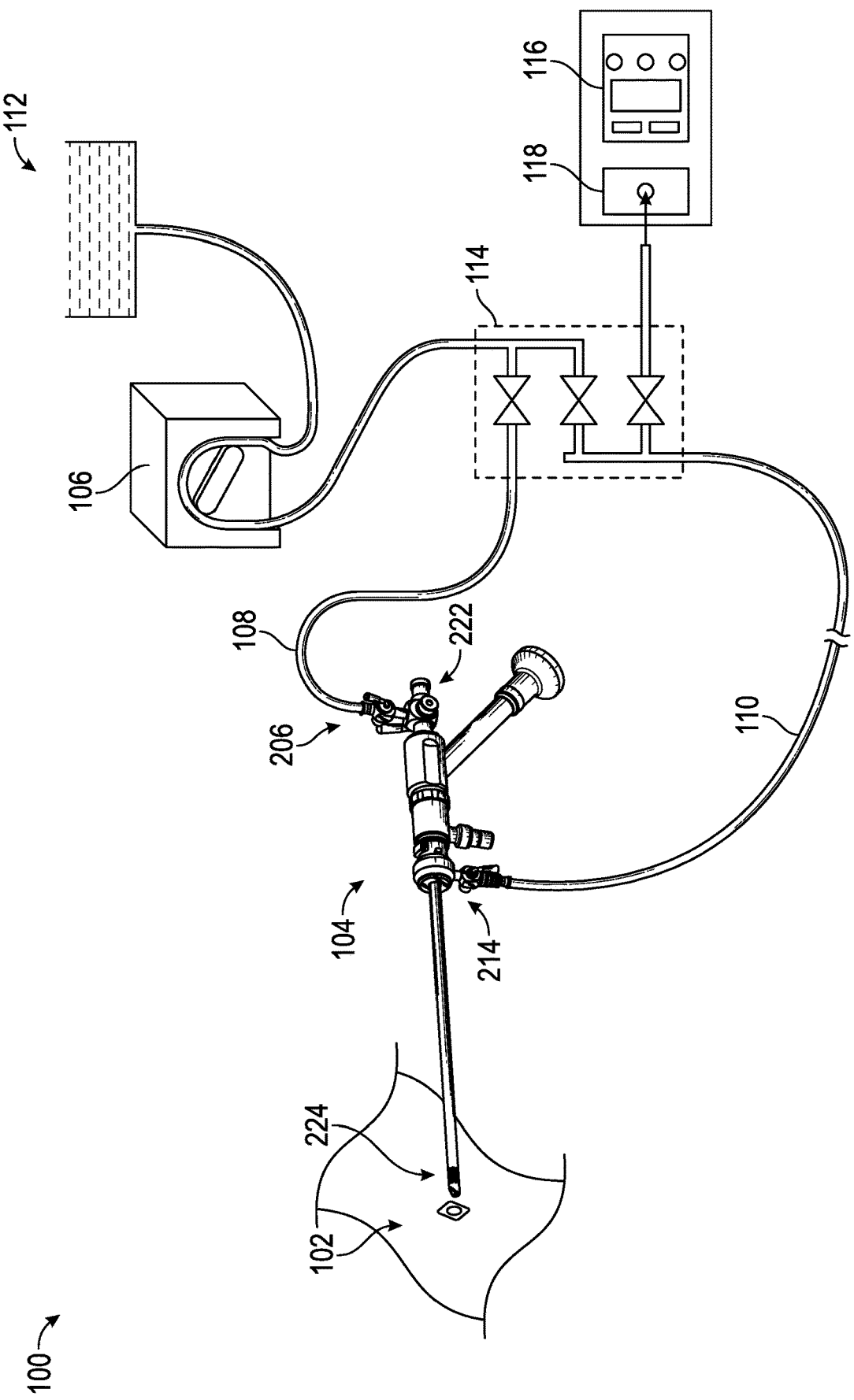
FIG. 1 shows a system in accordance with at least some embodiments.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

A "visualization conduit" shall mean a medium through which visualization takes place during use of an endoscope. The visualization conduit may be, for example, a rod lens or an optical fiber bundle. The fact that the visualization conduit can carry illumination to the viewing area shall not obviate the status as a visualization conduit.

A "light fiber bundle" shall mean a plurality of optical fibers through which light is carried to illuminate an area of visualization (the visualization through a separate visualization conduit). The fact that each optical fiber can theoretically be used to provide visualization, albeit of low resolution, shall not obviate the status a light fiber bundle (individually or as a group) as a light fiber bundle.

"Blunt front" shall mean an endoscope or sheath whose distal tip has only a single feature, and that single feature forms a plane perpendicular to a central axis of the endoscope or sheath.

"Coplanar," with respect to features of endoscopes, sheaths, or components that are assembled to construct an endoscope, shall also include parallel planes defined by the respective features where the perpendicular distance between the planes is 0.5 millimeters or less.

"Fluid bearing" shall mean a layer of fluid flowing into a volume between an outside surface of an endoscopic device (e.g., an endoscope and/or sheath) and an inside surface of an aperture into which the endoscopic device is inserted. The fluid bearing reduces the force of insertion of the endoscopic device relative to insertion of the endoscopic device without such fluid flowing.

"Endoscopic device" shall mean an endoscope alone, or a combination device comprising an endoscope telescoped within a sheath.

"Above," in relation to a fluid bag (e.g., saline bag) and a component, shall mean the fluid bag has a higher elevation than the recited component measured with respect to local gravity.

"Straight through-holes," in relation to the perforations disposed on the distal end of an endoscopic device, shall mean perforations where each perforation defines a central axis and the central axis defined by each perforation is perpendicular to a central axis of the endoscopic device.

"Angled through-holes," in relation to the perforations disposed on the distal end of an endoscopic device, shall mean perforations where each perforation defines a central axis and the central axis defined by each perforation is non-perpendicular to a central axis of the endoscopic device.

"Tapered through-holes," in relation to the perforations disposed on the distal end of an endoscopic device, shall mean perforations in the shape of conical frustums, where each perforation defines a central axis, a first bore on the outside surface of a sheath of the endoscopic device and a second bore on the inside surface of the sheath, and the central axis defined by each perforation may be perpendicular to a central axis of the endoscopic device or may be at an angle other than perpendicular to the central axis, and the first bore comprising a larger diameter than the second bore.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

A number of solutions are currently employed in endoscope design to decrease the insertion force. For example, an endoscopic device cross sectional diameter may be reduced in a design to decrease insertion force and pain, however, cross sectional diameter is practically limited by the endoscopic device's internal functional components. In addition, a number of tip features may be employed to decrease insertion force, including tapered or angled geometries to create a wedge effect. Other dilation instruments may be used to stretch the orifice prior to endoscopic device insertion, however a "blind entry" technique may result in undetected internal injuries, and over-dilation may cause leakage around the endoscopic device in procedures where distension media is employed. Biocompatible lubricants are sometimes used to reduce sliding friction between the tissue and the outer surface of the endoscopic device as it is advanced; lubricants can spread and contaminate other surfaces within the operating field. Moreover, in scenarios where the insertion force is relatively high, the lubricant may be ineffective.

In procedures such as hysteroscopy, where endoscopy is enabled by a distending fluid medium, a technique called "hydro-dilation" is employed to decrease the insertion force. As the endoscopic device is inserted, pressurized fluid is ejected from the distal tip of the endoscopic device, forcing the orifice to expand ahead of the endoscopic device as it is advanced. The hydro-dilation technique is effective in reducing the force employed to initially expand the orifice at the tip of the endoscopic device. However once the tip has passed through the orifice, the tissue is free to collapse around the outer surface of the endoscopic device and cause significant sliding friction forces and resultant tissue trauma, which may result in increased discomfort and healing time.

With the historical background in mind, the various example embodiments are directed to utilizing a fluid pumped through the endoscopic device and discharged at or near the insertion point, where the fluid acts as a linear bearing or a fluid bearing to reduce insertion force. Consider, as an example, the introduction of a pressurized fluid layer between the orifice and the outer surface of the endoscopic device as the endoscopic device is advanced, effectively creating a fluid bearing between the orifice and the endoscopic device. The fluid is introduced at a pressure great enough to interrupt the sliding friction contact between the endoscopic device and the tissue. The insertion force will therefore be governed instead by the shear forces induced in the fluid as the endoscopic device is advanced. At most fluid viscosities (except for extremely high viscosity), the insertion force will be significantly lowered from the insertion force used when the endoscopic device and tissue make sliding frictional contact. The example embodiments discussed herein make use of fluid (e.g., isotonic fluid like saline) which is already used for other reasons in various procedures. In contrast to hydro-dilation, the various example embodiments of forming a fluid bearing actively decrease the frictional force on the outer surface of the endoscopic device.

FIG. 1 shows a system 100 for creating a fluid bearing. In an embodiment, the system 100 comprises an endoscopic device 104, the distal tip 224 of which is inserted through an aperture 102; the endoscopic device 104 is connected to a fluid pump 106 and a fluid reservoir 112 (such as a saline bag). In various embodiments, the fluid pump 106 may comprise a rechargeable battery pack or may be coupled to a battery pack or a wall socket (not shown). It is appreciated that, in various embodiments, the fluid pump 106 may be fluidly coupled to a separate fluid reservoir 112, and in alternate embodiments the fluid pump 106 may comprise a fluid reservoir. The fluid pump 106 may in some embodiments be a peristaltic pump (as shown). In an embodiment where the fluid reservoir 112 is separate, it may be coupled to the pump 106 and/or the fluid line 108, or may be in direct fluid communication with the fluid port 206 and/or the fluid port 214.

In an embodiment, the pump 106 is coupled to the endoscopic device 104 by way of an inflow port 206 and a fluid port 214. The inflow port 206 is in fluid communication with a working channel (308 as shown in FIG. 3) and the pump 106 may supply fluid from the fluid reservoir to the working channel 308 by way of fluid line 108. For fluid inflow, fluid flows in a first direction from the proximal end 222 towards the distal end 224 of the endoscopic device 104. In an embodiment, using the buttons, switches, toggles, or other means on the pump 106, the user may control the flow of fluid to the working channel 308 (FIG. 3).

The pump 106 may also be fluidly connected via a second fluid line 110 to fluid port 214; the fluid port 214 may be in communication with a fluid path that may be used as discussed herein to form a fluid bearing. The fluid bearing may be formed when fluid is pumped via the second fluid line 110 by the pump 106 towards the distal end 224 of the endoscopic device 104 and exits through the distal end of the fluid path through apertures or other features as discussed more below. In some embodiments, the fluid flow may be toggled and reversed, for example, by way of one of a plurality of valves 114. By operation of the valves 114, the second fluid line 110 may also be coupled to a suction mechanism such as a suction wall pump 118, which may be a stand-alone feature or which may be part of a unit that may include a plurality of other controls for power, display, and adjustment of direction and rate of fluid flow. In an embodiment, the pump 106, which may comprise a peristaltic pump, a positive displacement pump, or a centrifugal pump, and the plurality of valves 114 may cause fluid to flow via the fluid line 110 to form a fluid bearing at the distal end 224 between the outer surface of the endoscopic device 104 and the inside surface of the aperture 102.

Figure 2:
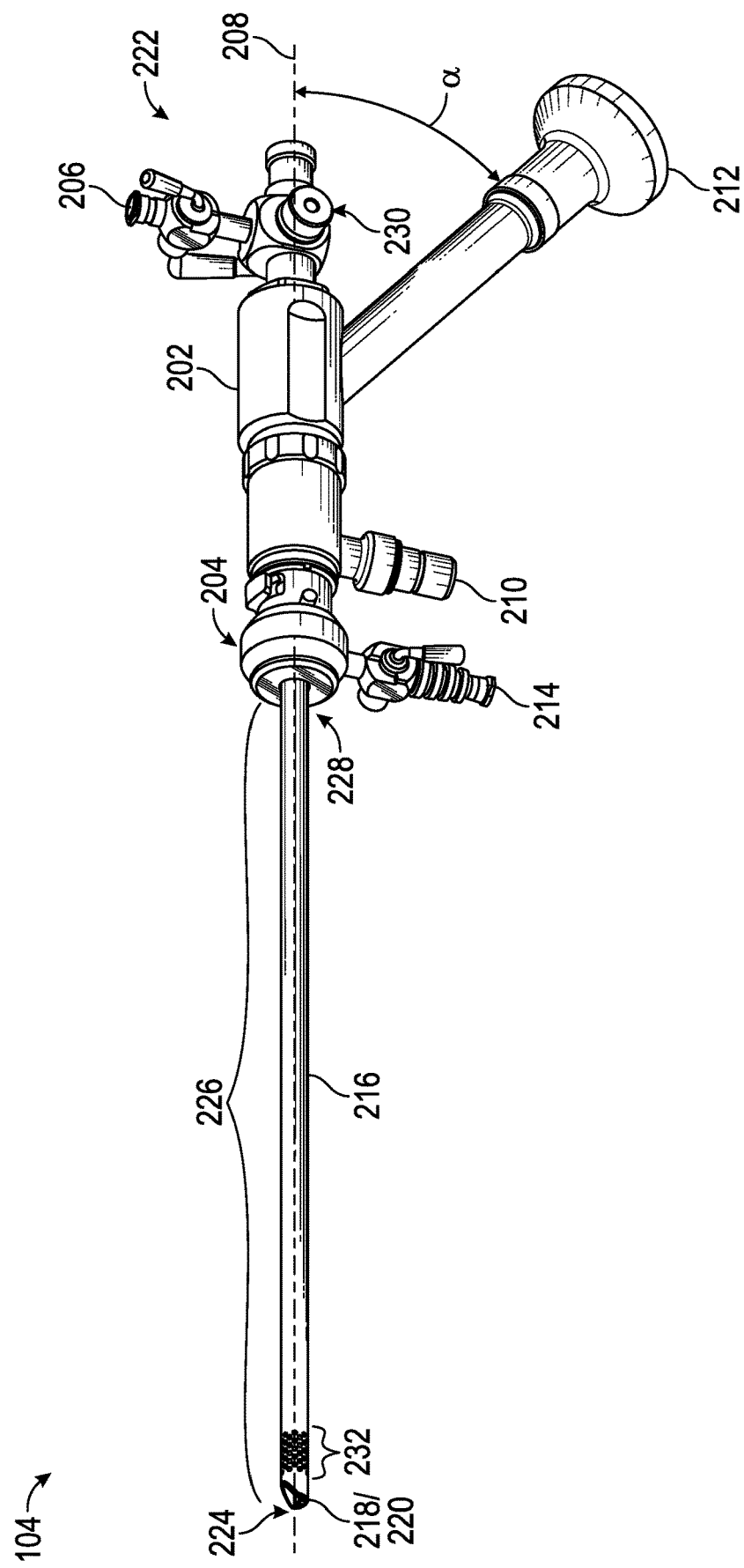
FIG. 2 shows a perspective view of an endoscopic device comprising an endoscope telescoped in a sheath in accordance with at least some embodiments.

FIG. 2 shows a perspective view of the endoscopic device 104 comprising an endoscope 202 telescoped in a sheath 204. FIG. 2 illustrates the endoscopic device 104 comprising a central axis 208, a proximal end 222, and a distal end 224 defined by the distal tips 218 of the endoscope 202 and 220 of the sheath 204. FIG. 2 also illustrates inflow port 206, and optics port 210 through which light may be provided to a light fiber bundle. The endoscopic device 104 may also comprise a viewing port 212 that may form an angle α which may be about 40 angular degrees as measured from the central axis 208 of the endoscopic device 104.

The viewing port 212 has disposed therein a visualization conduit (not shown) that extends from the viewing port 212 to the distal end 224. The endoscopic device 104 further comprises an elongated shaft 216 having a length 226 from a proximal end 228 of the elongated shaft 216 to the distal end 224. In an embodiment, the endoscope 204 and the sheath 202 may terminate at the distal end 224 along the same plane perpendicular to the central axis, and, in alternate embodiments, the sheath 204 may terminate a predetermined distance from the distal tip 218 of the endoscope as discussed more below. While perforations 232 are shown in FIG. 2, and are discussed in further detail below, depending upon the embodiment the perforations may or may not be employed.

In an embodiment, the elongated shaft 216 is coupled to an insertion valve 230, and in use various tools (e.g., shavers, ablation devices) may be telescoped into the first or working channel (not shown) of the elongated shaft 216 through the insertion valve 230. The sheath 204 comprises fluid port 214 located near the proximal end of the sheath 204. The fluid port 214, when the valve of the port is open, is in fluid communication with a fluid path, which may, in some embodiments, be referred to as an annular space or channel. The fluid path may be defined by an outside surface of the endoscope 202 and an inside surface of the sheath 204, as further illustrated in FIGS. 8A-8D.

Thus, fluid (e.g., as pumped by the fluid pump 106 shown in FIG. 1) may flow along the fluid path by way of the fluid port 214 and flow out distal end 224. In operation in accordance with example methods and systems, the fluid path may be used to introduce pressurized fluid during endoscopic device insertion; the fluid may be ejected radially through the perforations 232 as discussed more below or by other means. The fluid ejected creates a friction-reducing fluid film, referred to as a fluid bearing, between the sheath 204 and the tissue of an aperture through which the sheath 204 is inserted.

In some embodiments, the fluid may be ejected via the perforations 232 that may be referred to as bores or through-holes. These perforations 232 may be disposed radially along the outside surface of the sheath 204 and along a length of the distal tip 220. The perforations 232 may comprise straight through-holes, angled through-holes, and/ or tapered through-holes, or combinations thereof, and enable fluid flow through the fluid path either towards or away from the distal end 224. The perforations may be formed as round, elliptical, polygonal, or other shapes or combinations of various shapes, and may be approximately the same dimensions or may vary in dimension, depending upon the embodiment.

Figure 3A:
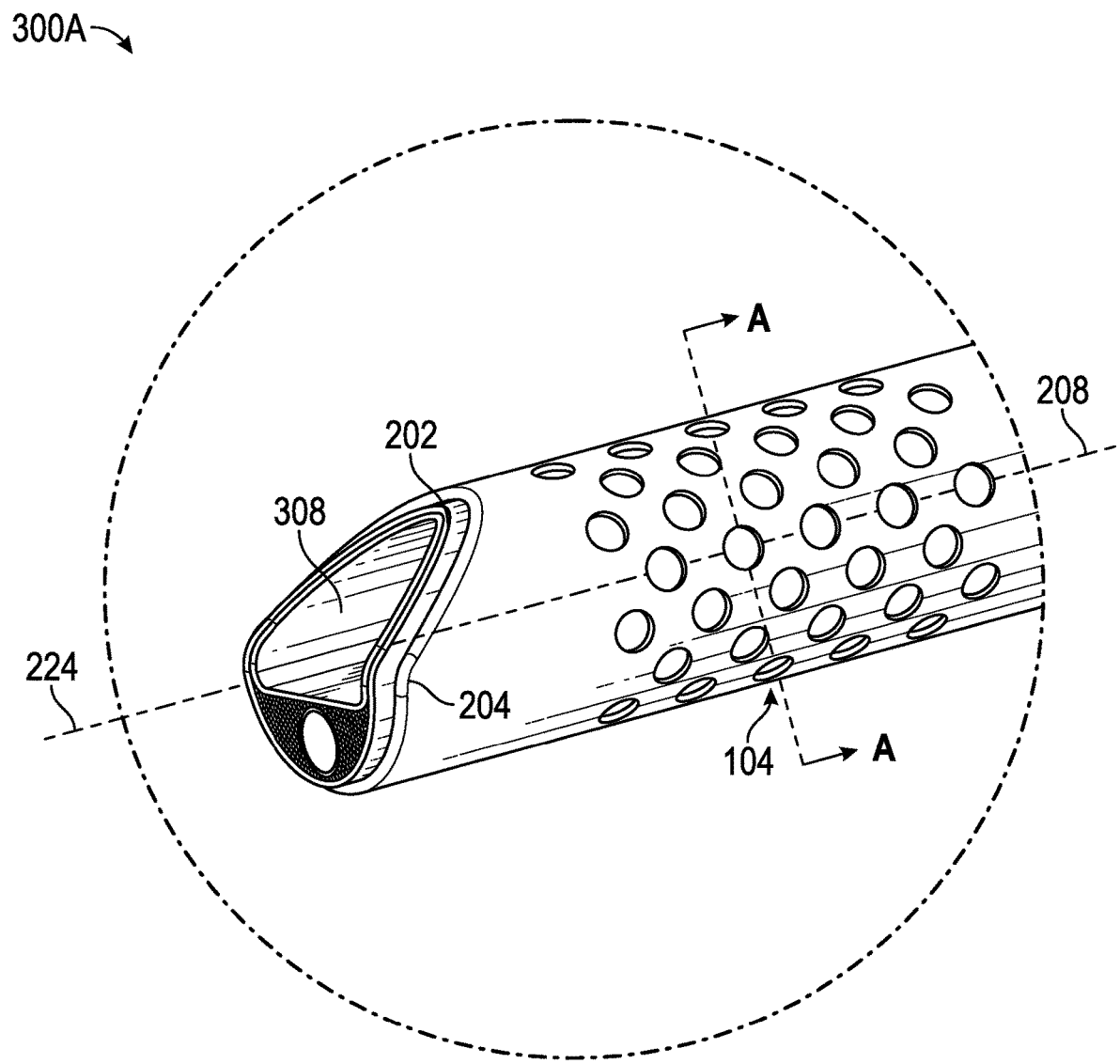
FIG. 3A shows a magnified perspective view of the distal end of an example endoscopic device in accordance with at least some embodiments.

FIG. 3A shows a magnified perspective view 300A of the distal end 224 of an example endoscopic device 104. In particular, FIG. 3 shows an example alignment of the sheath 204 and the endoscope 202 when the endoscope 202 is telescoped within the sheath 204. In some embodiments, and as shown, the sheath 204 may terminate near the distal end 224 of the endoscopic device 104. In an embodiment, a feature which may be used to create a fluid bearing is defined at the distal end 224 of the endoscopic device 104, an in the example shown the feature is the set of perforations 232. While an oblique tip is shown in FIG. 3A, the distal end 224 may comprise an oblique tip, a blunt tip, or other distal tip configurations.

Figure 3B:
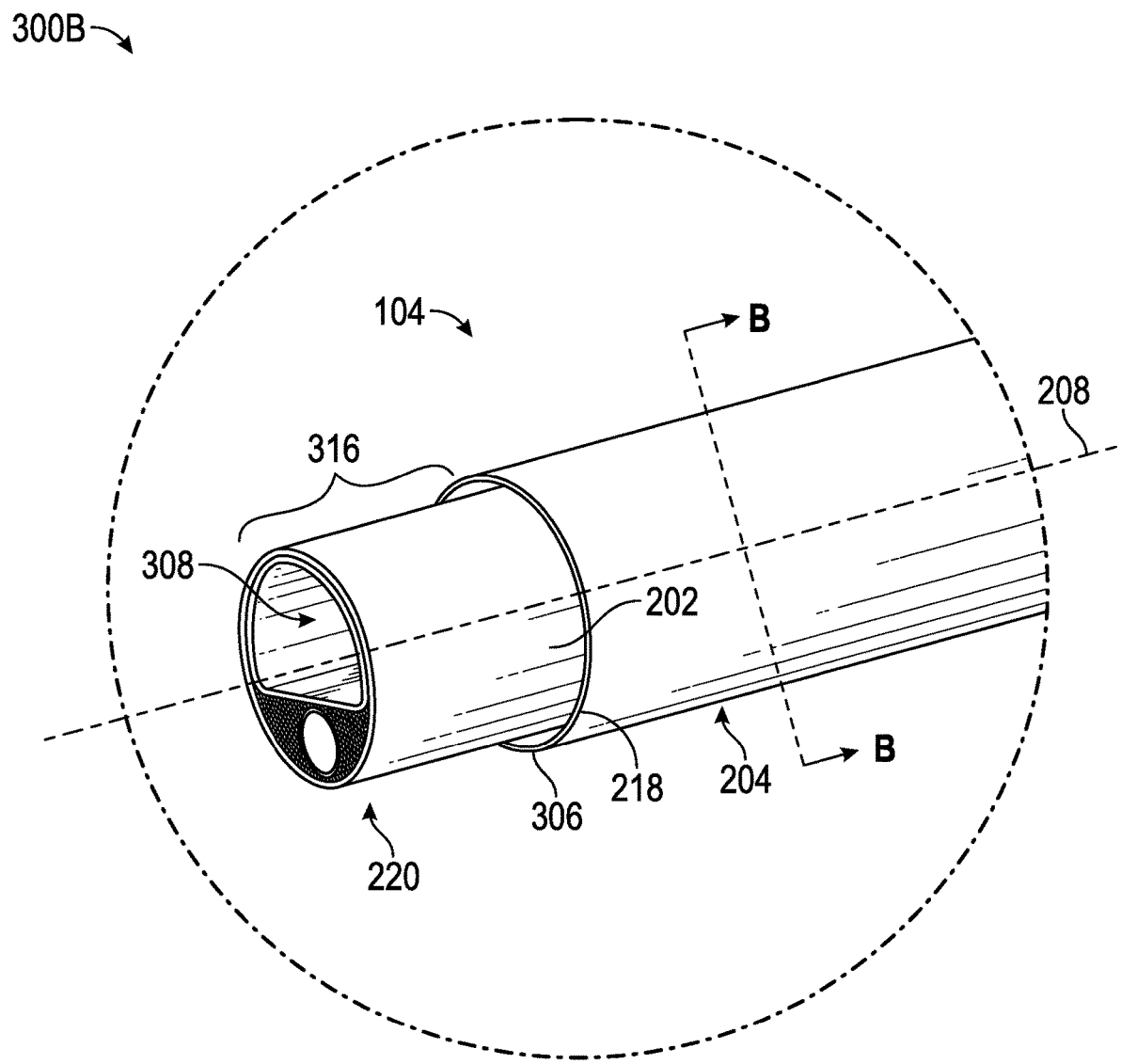
FIG. 3B shows a magnified perspective view of the distal end of an example endoscopic device in accordance with at least some embodiments.

FIG. 3B shows a magnified perspective view 300B of the distal end 224 of an example endoscopic device 104. In particular, FIG. 3B shows an example alignment of the sheath 204 and the endoscope 202 when the endoscope 202 is telescoped within the sheath 204. In embodiments as illustrated in FIG. 3B, the sheath 204 may comprise a discharge outlet or discharge port 306 located near the distal tip 220. Features such as the discharge port 306 may be employed to form a fluid bearing in example embodiments when the perforations are not employed. While a blunt tip is shown in FIG. 3B, the distal end 224 may comprise an oblique tip, a blunt tip, or other distal tip configurations. In embodiments shown in FIG. 3B the sheath 204 terminates (at its distal end 218) a predetermined distance 316 before the distal end 220 of the endoscope, as discussed more below.

Figure 4:
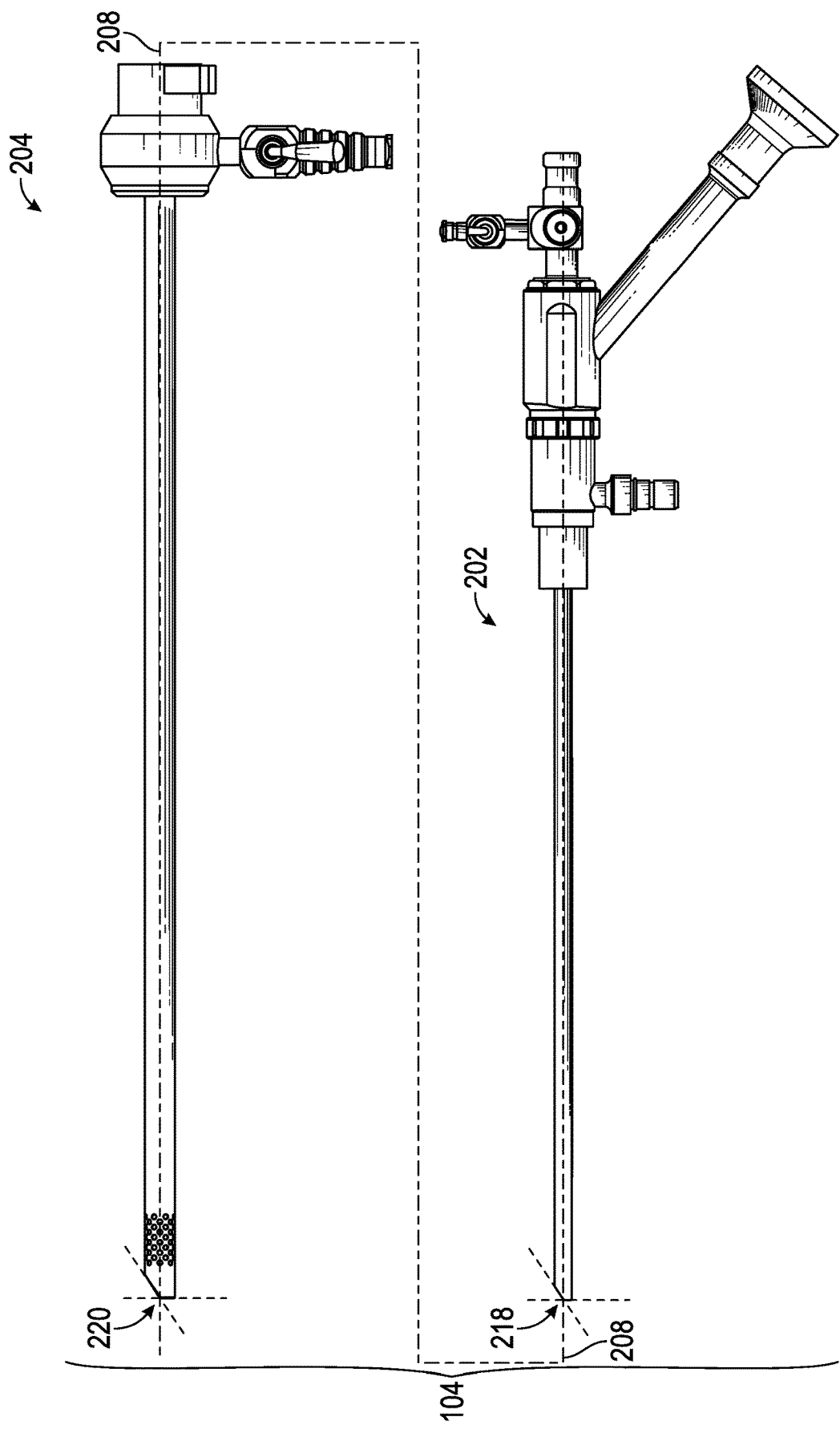
FIG. 4 shows an exploded view of each of the endoscope and the sheath, separately with the central axis along which both devices are aligned when the endoscope is telescoped within the sheath in accordance with at least some embodiments.

FIG. 4 shows an exploded view of each of the endoscope 202 and the sheath 204, separately with the central axis 208 along which both devices are aligned when the endoscope 202 is telescoped within the sheath 204. As discussed at least in the method in greater detail below, the endoscope 202 may be telescoped in the sheath 202 to form the endoscopic device 104.

Figure 5:
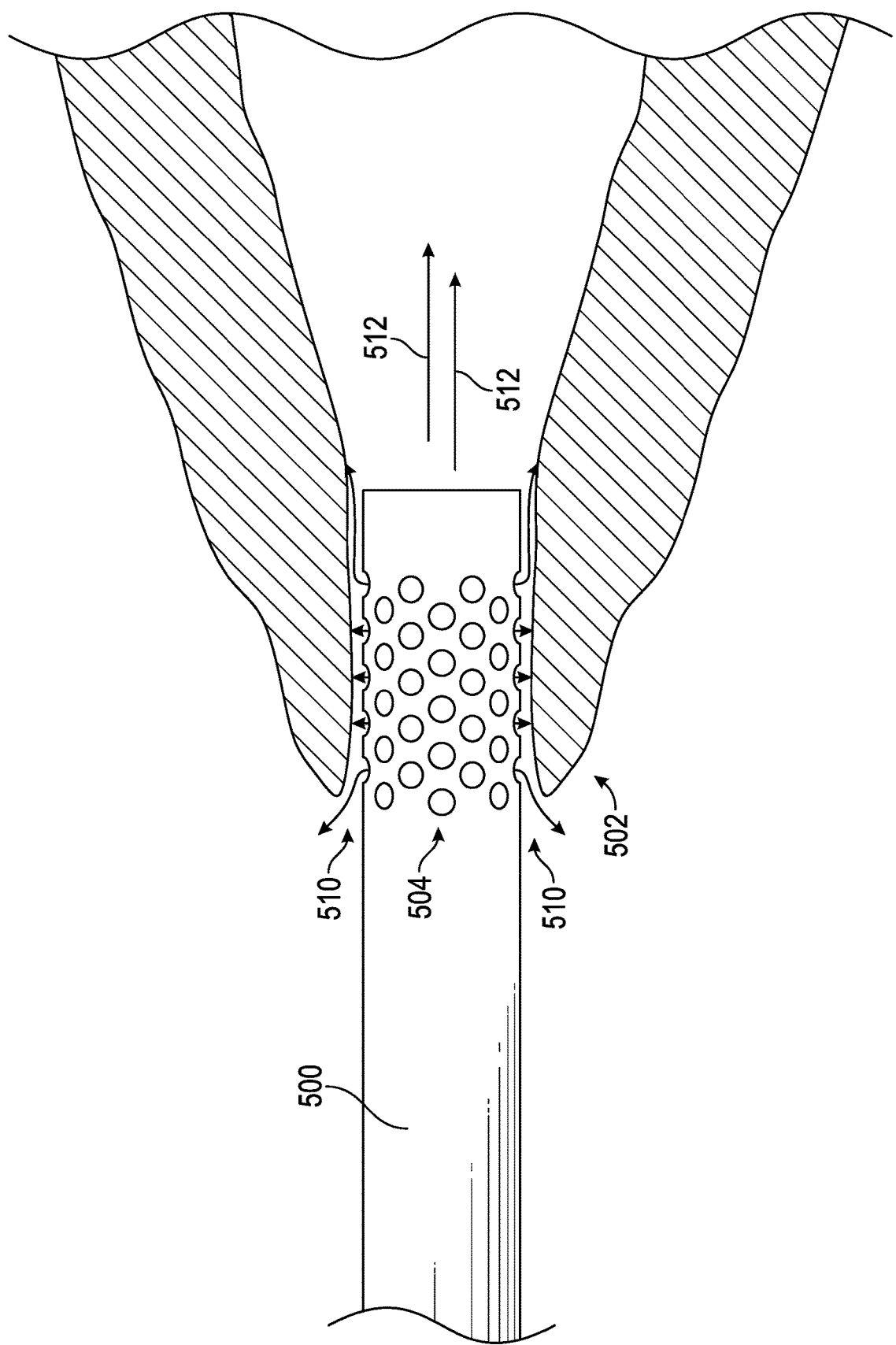
FIG. 5 shows an elevation view of the distal end of an endoscopic device in relationship to a cross-sectional view of an orifice, to show use of a fluid-bearing in accordance with at least some embodiments.

In various embodiments of the systems and methods discussed herein, a fluid bearing may be formed by establishing fluid flow axially or radially with respect to a central axis of the endoscopic device, and some of these embodiments are illustrated below in FIGS. 5-7. FIG. 5 shows an elevation view of the distal end of an endoscopic device in relationship to a cross-sectional view of an orifice, all to show use of a fluid-bearing. In particular, FIG. 5 shows an endoscopic device 500 being inserted into an orifice, such as the cervix 502. The endoscopic device 500 has perforations 504 out which fluid is pumped during insertion into the cervix 502. The flow of fluid creates a fluid bearing 510 around the distal tip of the endoscopic device 500 such that the inside diameter of the cervix 502 "rests" upon the fluid as the endoscopic device 500 is inserted. In the specific case of the uterus, the fluid bearing created by the fluid flowing out of the perforations 504 may be used in conjunction with hydro-dilation techniques (as illustrated by arrows 512). Fluid may be radially ejected through the perforations 504 in the endoscopic device's outer surface, as in the case described above with reference to FIG. 5. Although FIG. 5 shows the fluid being introduced through a series of perforations radially distributed about the endoscopic device, the fluid may be introduced by a number of different methods, components, and features.

Figure 6:
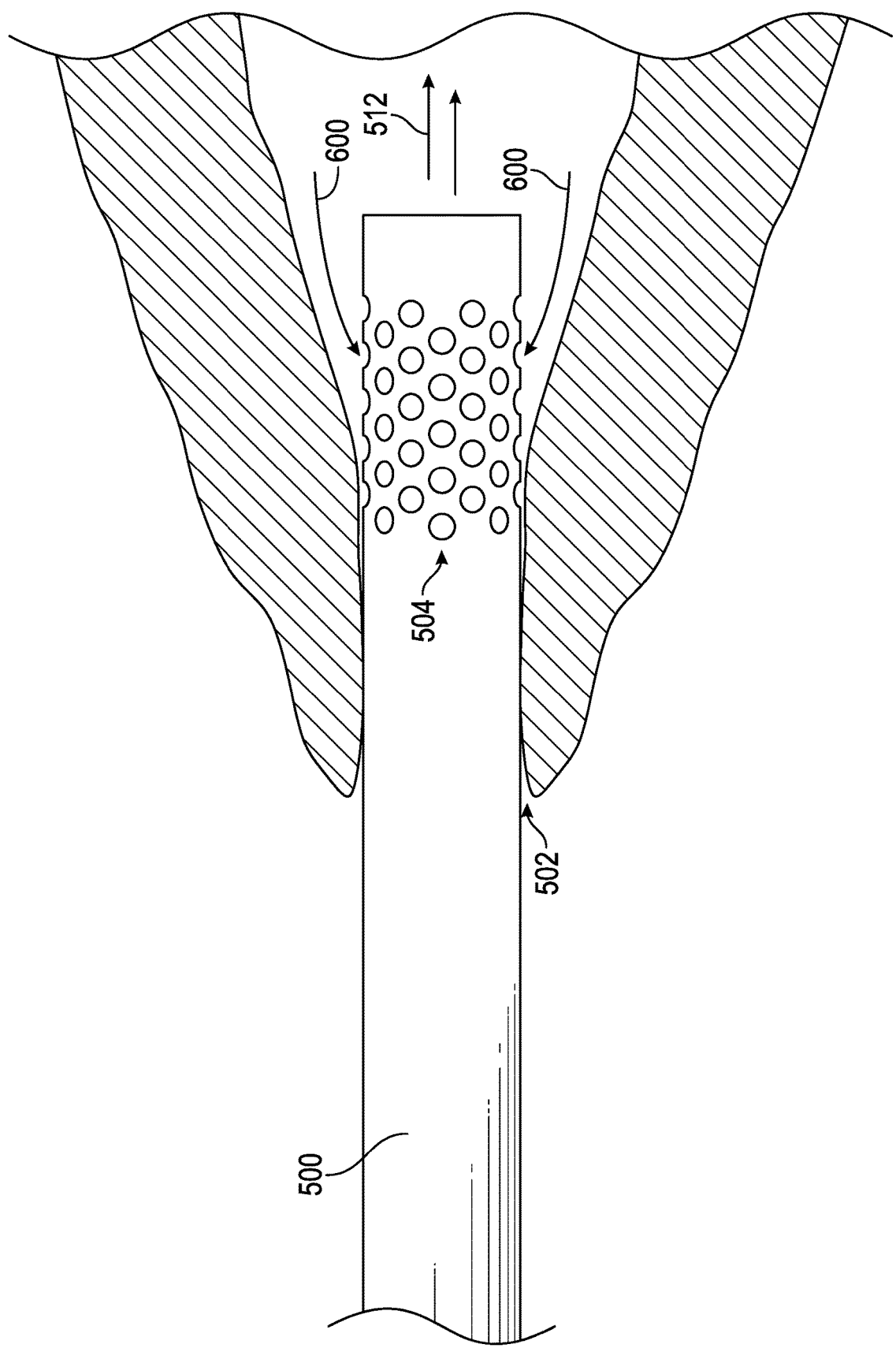
FIG. 6 shows an elevation view of the distal end of an endoscopic device in relationship to a cross-sectional view of an orifice, to show reversal of fluid flow in accordance with at least some embodiments.

FIG. 6 illustrates an elevation view of the distal end of an endoscopic device in relationship to a cross-sectional view of the cervix 502. In particular, FIG. 6 shows an endoscopic device 500 after insertion. After insertion, the fluid flow through perforations 504 may be reversed such that the perforations and flow path to which they fluid couple become the outflow channel for the surgical procedures. Thus, during the surgical procedure fluid may flow into the operative region (as shown the uterus) as shown by arrows 512, and fluid flows out through perforations and flow coupled thereto as shown by arrows 600. Thus, the perforations 504 may serve dual functions: first acting as a feature out which fluid flows during insertion to create the fluid bearing; and as an outflow path during the operative procedures.

Figure 7:
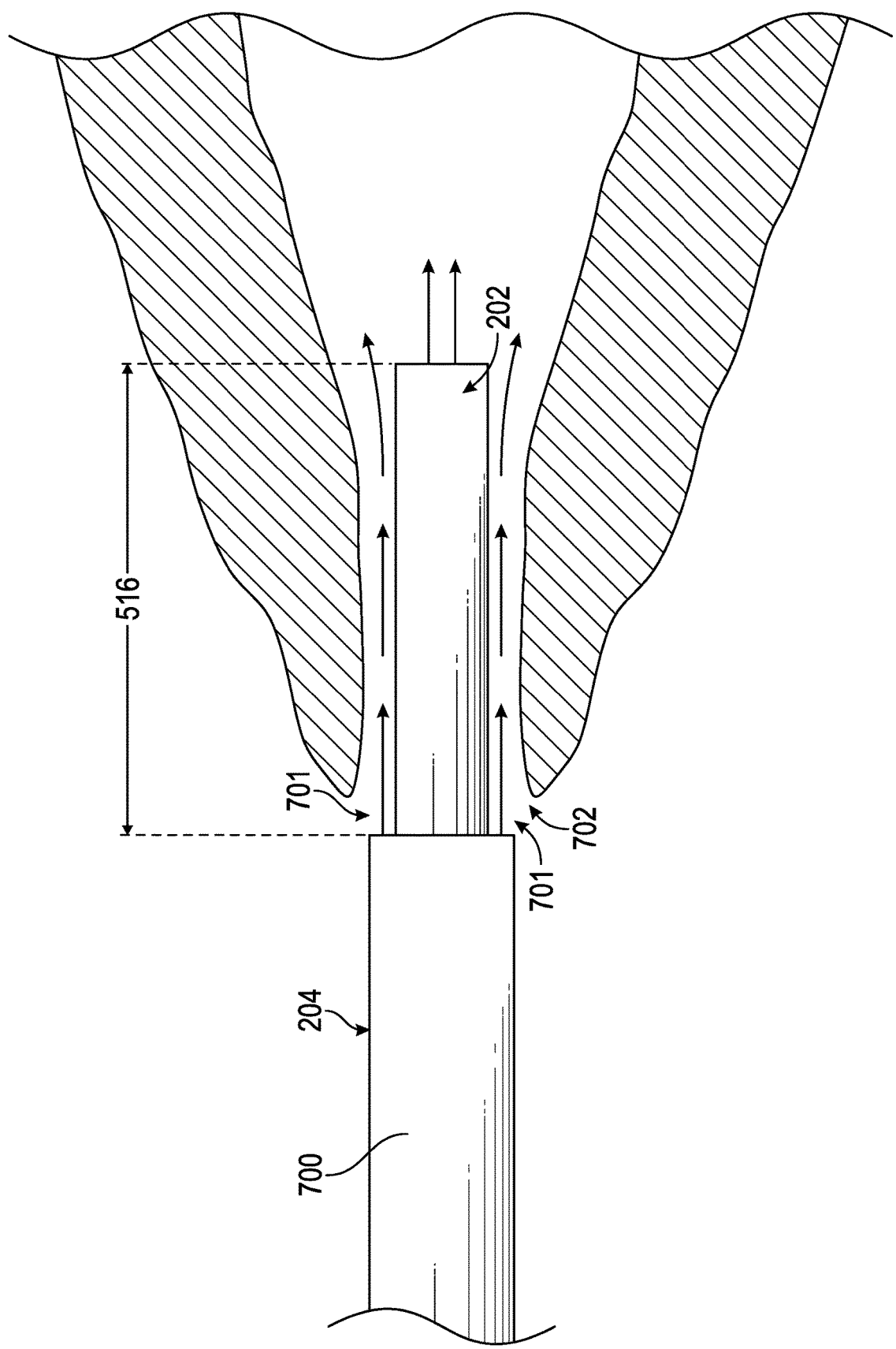
FIG. 7 shows an elevation view of the distal end of an endoscopic device in relationship to a cross-sectional view of an orifice, to show use of a fluid-bearing in accordance with at least some embodiments.

FIG. 7 shows an alternate embodiment for creation of the fluid bearing using the example system as shown in FIG. 3B. In particular, FIG. 7 shows an elevation view of the distal end of an endoscopic device in relationship to a cross-sectional view of an orifice, all to show use of a fluid-bearing. In FIG. 7 fluid is introduced by a feature of the endoscopic device that ejects or directs the fluid flow axially along the endoscopic device. In particular, the sheath 204 terminates prior to the termination of the endoscope, creating discharge port 306 (not visible in FIG. 7). The fluid flowing along the outside diameter of the endoscope 202 creates a fluid bearing 710 around a length of the distal tip of the device 700 such that the inside diameter of the cervix 702 "rests" upon the fluid of the fluid bearing as the endoscopic device 700 is inserted.

Figure 8A:
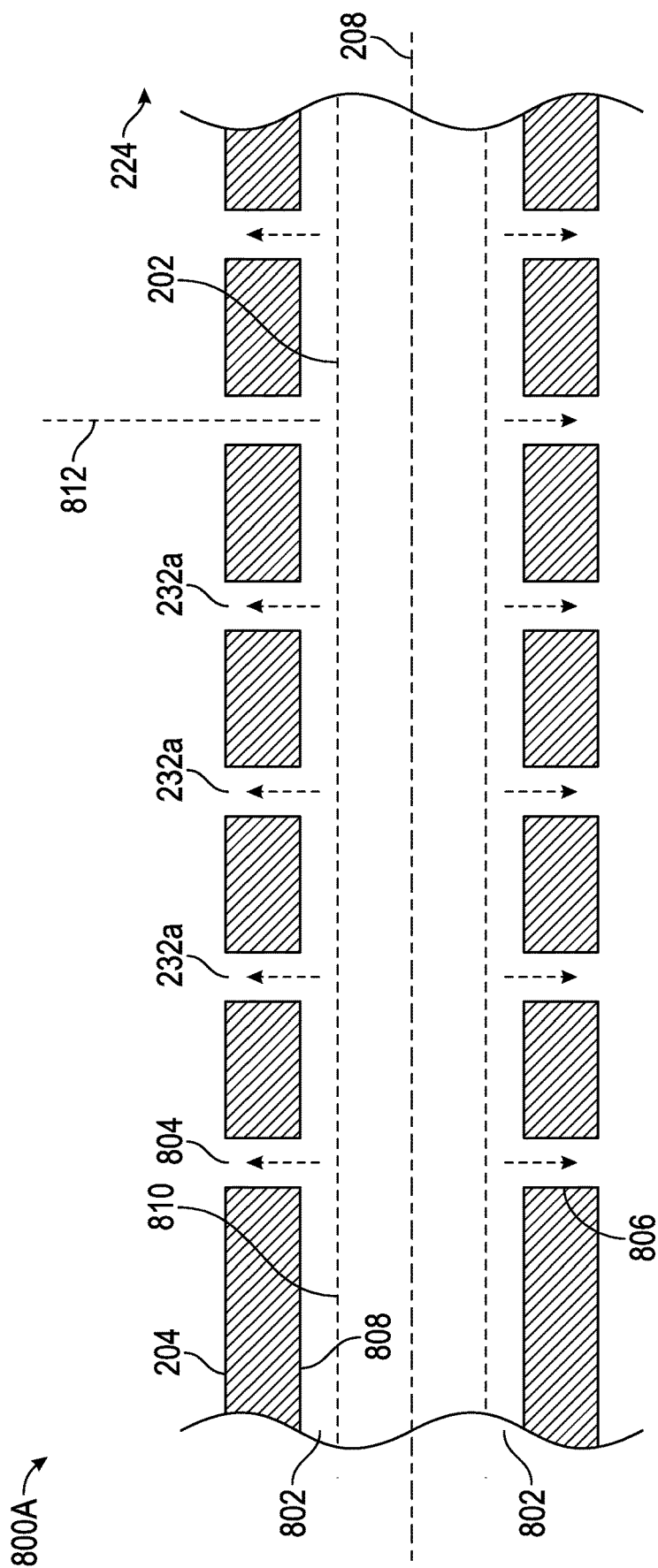
FIGS. 8A-8C are cross-sectional partial views of a distal tip of an endoscopic device taken along the center axis and illustrate various fluid bearings that may be employed to form a fluid bearing as discussed herein in accordance with at least some embodiments.
Figure 8B:
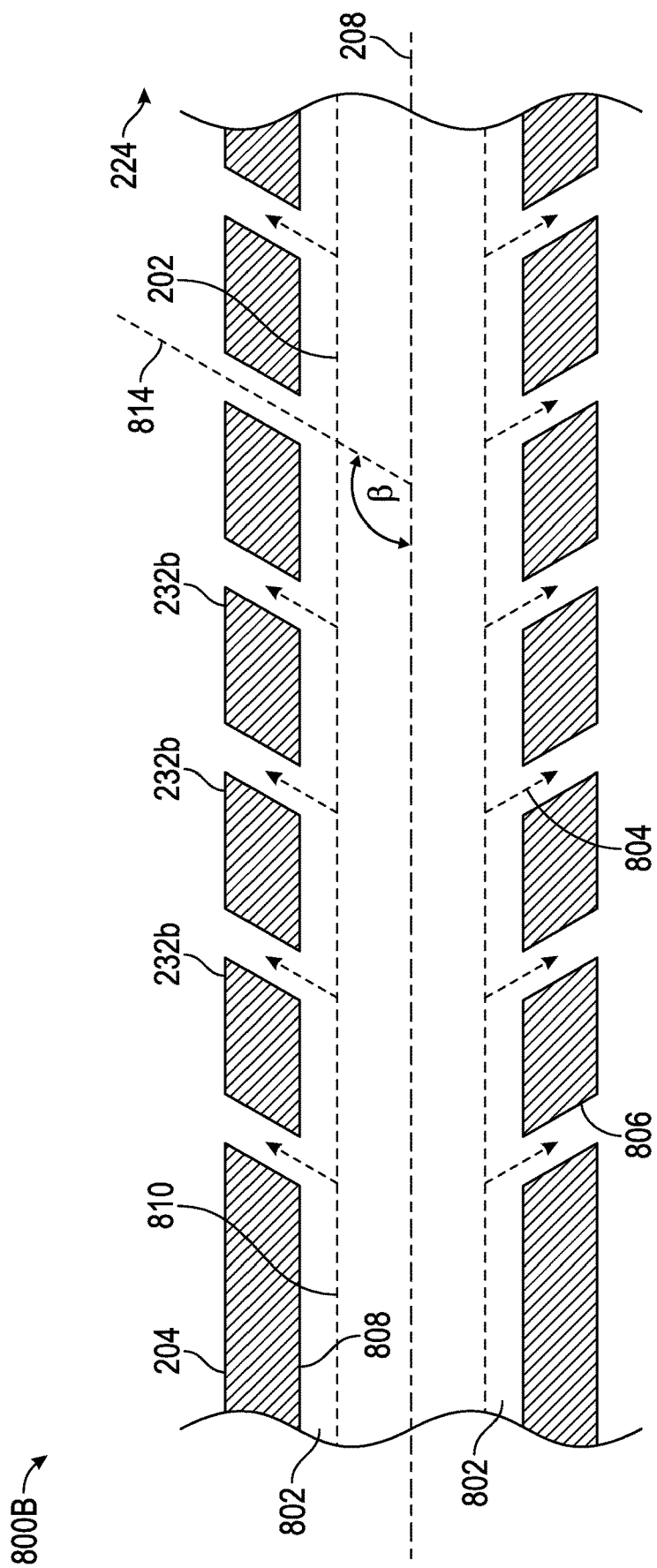
Figure 8C:
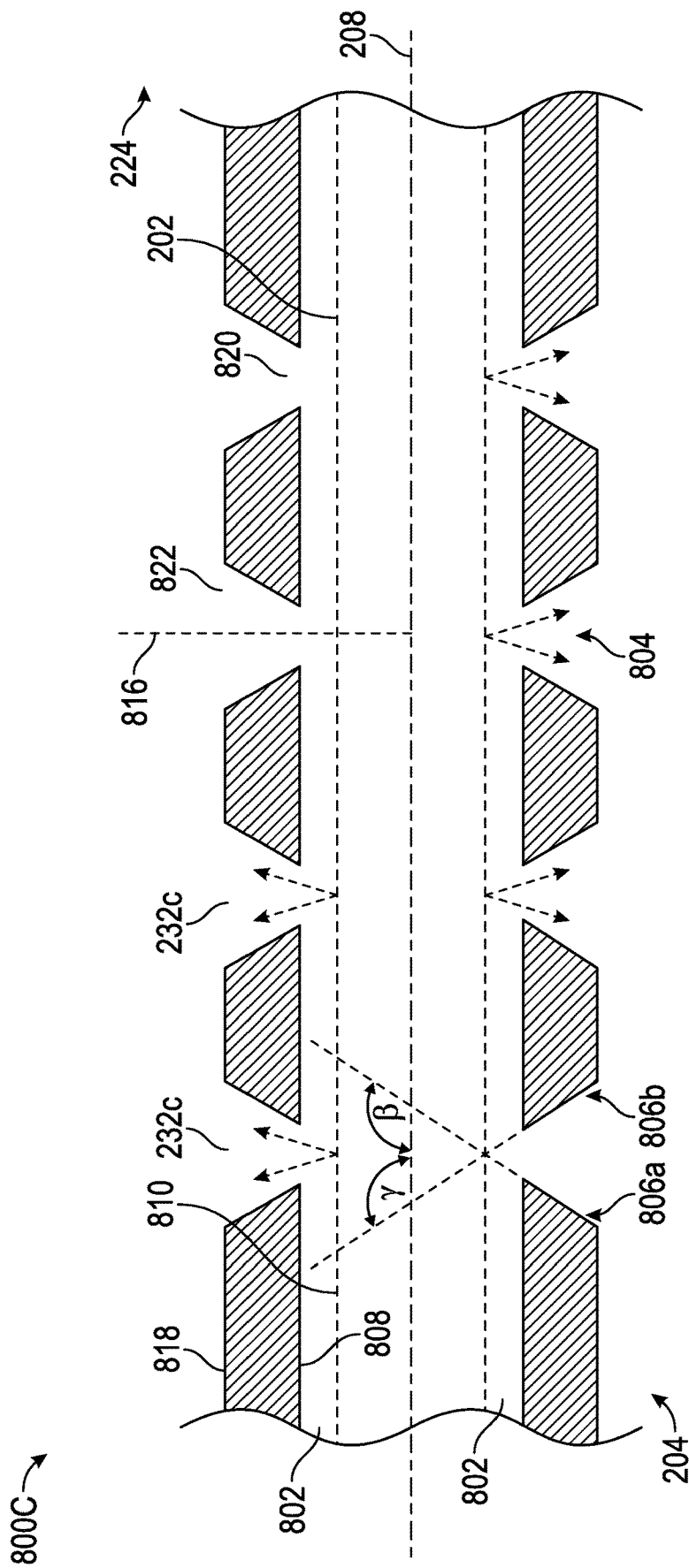
Figure 8D:
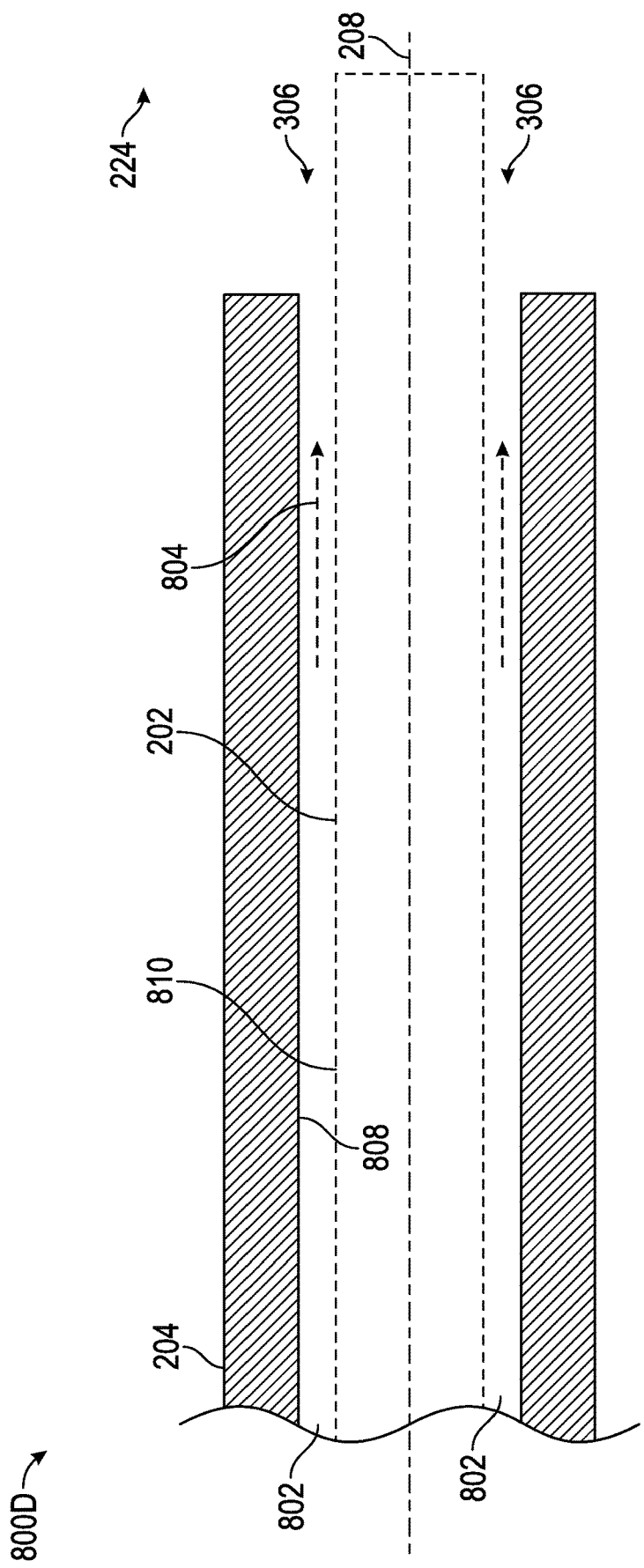
FIG. 8D is a magnified partial view of a distal tip of an endoscopic device taken along the center axis and illustrates a fluid bearing that may be employed to form a fluid bearing in accordance with at least some embodiments.

FIGS. 8A-8C are magnified partial cross-sectional views of a distal tip of an endoscopic device taken along the center axis and illustrate various embodiments that may be employed to form a fluid bearing as discussed herein. Elements such as working channels, optics and visualization channels, and related components are not illustrated in FIGS. 8A-8C so as not to unduly complicate the figures, but may be present in the endoscopic device discussed herein. FIGS. 8A-8B are cross-sections along a plane A-A that is perpendicular to the central axis 208, as discussed above with respect to FIG. 3A. FIG. 8A illustrates a partial cross-section 800A of a distal tip of an endoscopic device 104, taken along the central axis 208, that may be similar to the device 104 in FIG. 2. The fluid path 802, as also illustrated in FIGS. 8B-8D, is formed between an inside surface 808 of the sheath 204 and an outside surface 810 of the endoscope 202.

FIG. 8A illustrates a fluid path 802 that extends along the endoscopic device 104, as well as perforations 232A disposed radially around the sheath 204 along a predetermined portion of the length of the distal tip 220 of the sheath 204. The embodiment shown in FIG. 8A illustrates a plurality of straight through-holes, where the walls 806 of each through-hole (perforation 232) are parallel to each other and perpendicular to the central axis 208. In an embodiment, each perforation 232A defines a central axis 812 and the central axis 812 defined by each perforation is perpendicular to a central axis 208 of the endoscopic device 104. In an embodiment, fluid exits through the perforations 232B as indicated by the outflow arrows 804 in order to create the fluid bearing.

FIG. 8B illustrates a fluid path 802 that includes perforations 232A disposed radially around the sheath 204 along a predetermined portion of the length of the distal tip 220 of the sheath 204. In an embodiment, fluid exits through the perforations 232B as indicated by the outflow arrows 804 in order to create the fluid bearing. The embodiment shown in FIG. 8B illustrates a plurality of angled through-holes, where the walls 806 of each through-hole (perforation 232) are parallel to each other and each perforation 232B defines a central axis 814 which is at an angle β with respect to the central axis 208. The angle β may assist in fluid outflow 804 and the creation of the fluid bearing discussed herein. In an embodiment, fluid exits through the perforations 232B as indicated by the outflow arrows 804 in order to create the fluid bearing.

FIG. 8C illustrates a fluid path 802 including tapered through-hole perforations 232C disposed radially around the sheath 204 along a predetermined portion of the length of the distal tip 220 of the sheath 204. In an embodiment, fluid exits through the perforations 232C as indicated by the outflow arrows 804 in order to create the fluid bearing. Each tapered through-hole of the perforations 232C is shaped like a conical frustum and defines a central axis 816, a first bore 822 on the outside surface 818 of a sheath 204 of the endoscopic device and a second bore 820 on the inside surface 808 of the sheath, as well as a smooth transition (e.g., the walls 806) between the first bore 822 and the second bore 820. In an embodiment, each perforation 232C may define a central axis 816, which is shown as being perpendicular to the central axis 208 in FIG. 8C, but which may be at angles other than 90 degrees in various embodiments.

The embodiment shown in FIG. 8C illustrates a plurality of tapered through-holes, where the walls 806 of each through-hole (perforation 232C) are angled (not parallel) to each other, a first wall 806A may be at an angle β with respect to the central axis 208, and a second wall 806B may be at an angle γ with respect to the central axis 208. In an embodiment, angles β and γ may be equal, and, in other embodiments, the respective angles may be different. The angles β and γ may assist in fluid outflow 804 and the creation of the fluid bearing discussed herein.

FIG. 8D is a magnified partial view of a distal tip of an endoscopic device taken along the center axis and illustrates an embodiment that may be employed to form a fluid bearing as discussed herein. Elements such as working channels, optics and visualization channels, and related components are not illustrated in FIG. 8D so as not to unduly complicate the drawing, but may be present in the endoscopic device discussed herein. FIG. 8D illustrates a fluid path 802, as well as the endoscope 202 extending beyond the sheath 204 at the distal end 224. In embodiment shown, fluid exits through the distal end 224 by way of the discharge port 306 as indicated by the outflow arrows 804 in order to create the fluid bearing (e.g., as illustrated in FIG. 7).

Figure 9:
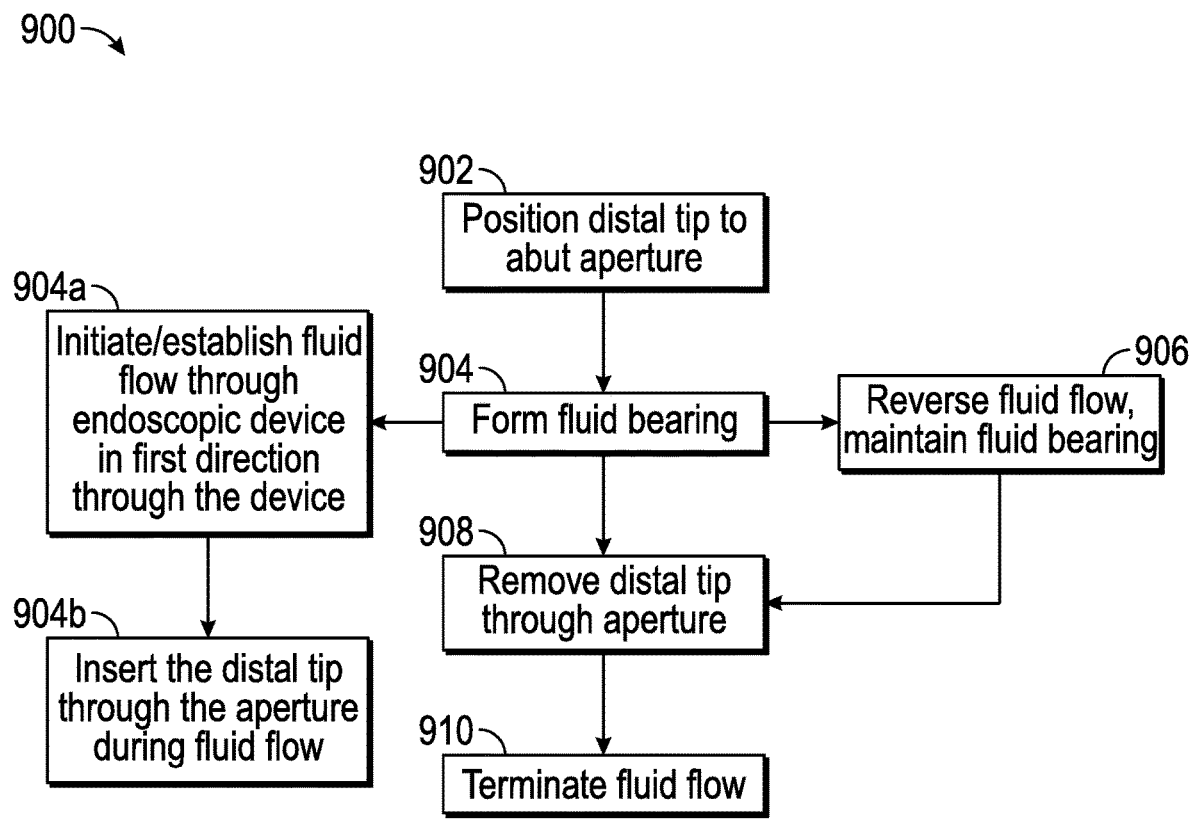
FIG. 9 is a flow chart for a method of forming a fluid bearing in accordance with at least some embodiments.

FIG. 9 illustrates a method 900 of performing a surgical procedure using a fluid bearing. At block 902 of the method 900, a distal tip of an endoscopic device such as that described in FIGS. 1-8D is positioned to abut an aperture into an operative cavity such as a patient's body. At block 904, a fluid bearing is formed between an inside surface of the aperture and an outside surface of the distal end of the endoscopic device. The fluid bearing may be formed at block 904 when a fluid flow is established at block 904a in a first direction. The distal tip is inserted at block 904b through the aperture during the fluid flow. In an embodiment, the fluid flow is established at block 904a in a first direction from a proximal end of the endoscopic device. The fluid flow may be established through a fluid path including the perforations that may be disposed radially along a length of a first portion of a distal end of the endoscopic device. The perforations are in fluid communication with the fluid path within the endoscopic device.

In an embodiment, forming the fluid bearing at block 904 further comprises pumping fluid from a fluid source through the outflow (fluid) path, the fluid flowing radially outward through the perforations. In an alternate embodiment, forming the fluid bearing at block 904 further comprises pumping fluid through the fluid path and the perforations, the fluid flow through the perforations having an axial component relative to a central axis of the endoscopic device. In another embodiment, forming the fluid bearing at block 904 bearing further comprises pumping fluid through the fluid path and then axially along the outside surface of the endoscopic device relative to a central axis of the endoscopic device. In various embodiments, the perforations further comprise at least one selected from the group consisting of: straight through-holes, angled through-holes, and tapered through-holes, as discussed at least in FIGS. 8A-8C. In an embodiment, positioning the endoscopic device at block 902 further comprises positioning the endoscopic device comprising an endoscope telescoped within a sheath, and where the perforations reside at the distal end of the sheath.

In an embodiment, the method 900 may comprise, at block 902, positioning the distal tip of a endoscopic device to abut an aperture into an operative cavity, and, in this embodiment, the endoscopic device comprises an endoscope telescoped within a sheath, the endoscope and sheath define a fluid path along a fluid path between an interior surface of the sheath and an exterior surface of the endoscope, and the endoscope and sheath define a discharge outlet circumscribing the endoscope at a distal tip of the sheath. At block 904, a fluid bearing is formed between an inside surface of the aperture and an outside surface of the endoscopic device by establishing a fluid flow along the fluid (outflow) path and out through the discharge outlet; at block 904a and inserting at least a first portion of the distal end of the endoscopic device through the aperture as the fluid flows through the discharge outlet at block 904b. It is appreciated that, in some embodiments, the first direction discussed at block 904a may be from a proximal end of the endoscopic device to the distal end, and that, in alternate embodiments, the first direction may be from a distal end of the endoscopic device towards the proximal end.

In some embodiments, at block 906, after insertion at block 904b, the method may further comprise reversing the flow of fluid along the fluid path during at least a portion of the surgical procedure. At block 908, the distal tip may be removed through the aperture while the fluid bearing is maintained, and at block 910, the fluid flow may be terminated. In some embodiments, at block 904a, establishing the fluid flow along the fluid path further comprises providing fluid to the fluid path by way of at least one selected from the group consisting of: a peristaltic pump, a positive displacement pump, a fluid bag disposed above the fluid port, and a centrifugal pump. In various embodiments, the working inflow and outflow channels discussed herein may be used in conjunction with the fluid path via which the fluid bearing is created.

The above discussion is meant to be illustrative of the principles and various embodiments of the present invention. Numerous variations and modifications will become apparent to those skilled in the art once the above disclosure is fully appreciated. For example, various combinations of perforations types, number, geometry, and size may be employed in different embodiments and may be employed along varying lengths of the endoscopic device. It is intended that the following claims be interpreted to embrace all such variations and modifications.

What is claimed is:

1. A method of performing a surgical procedure, comprising:
    positioning a distal tip of an endoscopic device to abut an aperture into an operative cavity, the endoscopic device defines perforations disposed along a length of a first portion of a distal end of the endoscopic device, and the perforations in fluid communication with a fluid path within the endoscopic device;

forming a fluid bearing radially around a circumference of the endoscopic device between an inside surface of the aperture and an outside surface of the distal end of the endoscopic device by:
  establishing a fluid flow along the fluid path and through the perforations; and
  inserting at least the first portion of the distal tip of the endoscopic device through the aperture as the fluid flows through the perforations by advancing the endoscopic device through the fluid bearing.

2. The method of claim 1 wherein positioning the endoscopic device further comprises positioning the endoscopic device comprising an endoscope telescoped within a sheath, and where the perforations reside at a distal end of the sheath.

3. The method of claim 1, wherein forming the fluid bearing further comprises pumping fluid from a fluid source through the fluid path and the perforations, the fluid flowing radially outward through the perforations.

4. The method of claim 1, wherein forming the fluid bearing further comprises pumping fluid through the fluid path and the perforations, the fluid flow through the perforations having an axial component relative to a central axis of the endoscopic device.

5. The method of claim 1, wherein forming the fluid bearing further comprises pumping fluid through the fluid path and then axially along the outside surface of the endoscopic device relative to a central axis of the endoscopic device.

6. The method of claim 1, wherein the fluid path is defined by an annular space between an interior surface of a sheath and an exterior surface of an endoscope telescoped in the sheath.

7. The method of claim 6, further comprising, after insertion, reversing the flow of fluid along the annular space for the surgical procedure.

8. The method of claim 1, wherein the perforations further comprises at least one selected from the group consisting of: straight through-holes; angled through-holes; and tapered through-holes.

9. The method of claim 1, wherein the fluid bearing is formed by an interaction between a fluid of the fluid bearing and the inside surface of the aperture to reduce friction between the endoscopic device and the inside surface of the aperture.

10. A method of performing a surgical procedure, comprising:
  positioning a distal tip of an endoscopic device to abut an aperture into a patient's body, the endoscopic device defines perforations disposed along a length of a first portion of a distal end of the endoscopic device, and the perforations in fluid communication with a fluid path within the endoscopic device;
  forming a fluid bearing radially around a circumference of the endoscopic device between an inside surface of the aperture and an outside surface of the distal end of the endoscopic device, the forming by:
    establishing a fluid flow along the fluid path and through the perforations; and
    inserting at least the first portion of the distal tip of the endoscopic device through the aperture as the fluid flows through the perforations by advancing the endoscopic device through the fluid bearing.

11. The method of claim 10 wherein positioning the endoscopic device further comprises positioning the endoscopic device comprising an endoscope telescoped within a sheath, and where the perforations reside at the distal end of the sheath.

12. The method of claim 10, wherein forming the fluid bearing further comprises pumping fluid from a fluid source through the fluid path and the perforations, the fluid flowing radially outward through the perforations.

13. The method of claim 10, wherein forming the fluid bearing further comprises pumping fluid through the fluid path and the perforations, the fluid flow through the perforations having an axial component relative to a central axis of the endoscopic device.

14. The method of claim 10, wherein forming the fluid bearing further comprises pumping fluid through the fluid path and then axially along the outside surface of the endoscopic device relative to a central axis of the endoscopic device.

15. The method of claim 10, further comprising, after insertion, reversing the flow of fluid along an annular space between an interior surface of a sheath and an exterior of an endoscope telescoped in the sheath for the surgical procedure.

* * * * *